United States Patent
Ozeran et al.

(10) Patent No.: US 11,742,064 B2
(45) Date of Patent: Aug. 29, 2023

(54) AUTOMATED QUALITY ASSURANCE TESTING OF STRUCTURED CLINICAL DATA

(71) Applicant: TEMPUS LABS, INC., Chicago, IL (US)

(72) Inventors: Jonathan Ozeran, Chicago, IL (US); Chris Brenner, Chicago, IL (US)

(73) Assignee: TEMPUS LABS, INC., Chicago, IL (US)

( * ) Notice: Subject to any disclaimer, the term of this patent is extended or adjusted under 35 U.S.C. 154(b) by 172 days.

(21) Appl. No.: 16/732,210

(22) Filed: Dec. 31, 2019

(65) Prior Publication Data

US 2020/0279623 A1  Sep. 3, 2020

Related U.S. Application Data

(60) Provisional application No. 62/787,249, filed on Dec. 31, 2018.

(51) Int. Cl.
| | |
|---|---|
| G16H 10/60 | (2018.01) |
| G16H 10/40 | (2018.01) |
| G16H 15/00 | (2018.01) |
| G16H 50/20 | (2018.01) |
| G16H 10/20 | (2018.01) |
| G06F 16/215 | (2019.01) |

(52) U.S. Cl.
CPC .......... *G16H 10/60* (2018.01); *G06F 16/215* (2019.01); *G16H 10/20* (2018.01); *G16H 10/40* (2018.01); *G16H 15/00* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 10,395,772 B1 | 8/2019 | Lucas | |
| 2004/0189708 A1 | 9/2004 | Larcheveque | |
| 2005/0234740 A1* | 10/2005 | Krishnan | ......... G06Q 10/06398 |
| | | | 705/2 |
| 2007/0239376 A1* | 10/2007 | Reiner | ............. G06Q 10/06395 |
| | | | 702/84 |

(Continued)

FOREIGN PATENT DOCUMENTS

| | | |
|---|---|---|
| CN | 101714191 A | 5/2010 |
| WO | 2018224937 A1 | 12/2018 |

OTHER PUBLICATIONS

International Searching Authority, International Search Report and Written Opinion for application PCT/US2019/069156, dated Mar. 18, 2020.

(Continued)

*Primary Examiner* — Joshua B Blanchette
*Assistant Examiner* — Andrew E Lee
(74) *Attorney, Agent, or Firm* — MARSHALL, GERSTEIN & BORUN LLP

(57) ABSTRACT

A method for checking the quality of data content in a structured clinical record is disclosed. The method may include the steps of providing a data quality test that checks the content of at least a portion of the data content in the structured clinical record, applying the data quality test to the portion of the data content, and returning the results of the data quality test.

30 Claims, 17 Drawing Sheets

(56) References Cited

U.S. PATENT DOCUMENTS

| | | | |
|---|---|---|---|
| 2011/0276346 A1* | 11/2011 | Reiner | G16H 40/20 |
| | | | 705/3 |
| 2013/0346101 A1 | 12/2013 | Kahn et al. | |
| 2014/0278448 A1* | 9/2014 | Sadeghi | G16H 15/00 |
| | | | 705/2 |
| 2016/0321559 A1* | 11/2016 | Rose | G06N 10/00 |
| 2017/0053074 A1* | 2/2017 | Enzmann | G06Q 10/103 |
| 2017/0185720 A1* | 6/2017 | Downs | G16H 50/50 |
| 2019/0005012 A1* | 1/2019 | Priestas | G06F 40/295 |
| 2019/0156947 A1* | 5/2019 | Nakamura | G16H 50/20 |
| 2020/0126663 A1 | 4/2020 | Lucas | |
| 2021/0043275 A1* | 2/2021 | Landau | G06Q 10/06398 |
| | | | 705/2 |
| 2021/0108255 A1* | 4/2021 | Dietrich | G06N 10/00 |

OTHER PUBLICATIONS

U.S. Appl. No. 16/702,510, "Clinical Concept Identification, Extraction, and Prediction System and Related Methods", filed Dec. 3, 2019.

U.S. Appl. No. 16/657,804, "Data Based Cancer Research and Treatment Systems and Methods", filed Oct. 18, 2019.

* cited by examiner

FIG. 1

| condition_occurrence_id | person_id | condition_concept_id | condition_start | condition_end | condition_type_concept_id | visit_occurrence_id | condition_source_value | condition_source_concept_id |
|---|---|---|---|---|---|---|---|---|
| 123456789 | ABC123DEF456 | 35206182 | 7/25/17 | 7/25/17 | 44786627 | 465504872 | C32.9 | 799289 |

FIG. 2

| drug_concept_id | person_id | drug_exposure_start | drug_exposure_end | drug_source_value | drug_source_concept_id | route_source_value | dose_source_value | dose_unit_source_value |
|---|---|---|---|---|---|---|---|---|
| 45329886 | ABC123DEF456 | 7/28/17 | 7/28/17 | PACLITAXEL 6 MG/ML CONCENTRATE, IV | 72370 | intravenous | | ml |

TEMPUS

Patients | Projects | Templates | Value Sets aass sss | 815e3d87-93e0-4eee-9485-f3e33345b4ff      Q - [100] +    All Changes Saved | Pause Session Demographics
Diagnosis
Treatments and Outcomes
Genetic Testing and Labs
DOCUMENTS  STRUCTURED DATA Demographics
Gender
○ Male ○ Female
Race
[Caucasian] [RH]
Date of birth
[MM ▼] [DD ▼] [YYYY ▼]
Date of death
[MM ▼] [DD ▼] [YYYY ▼]
Smoking status
[ ▼] [RH]
Cormobidities
[ ▼]
Menopausal status
[ ▼]
Gravidity
[ ▼]

Smoking Status

| Smoker • ✓ [RH] |
| 09/10/2018 |

| Smoker • [RH] |
| 08/10/2017 |

| Smoker • [NH] |
| 08/10/2015 |

[Apply]

| HD-DOC.pdf | D-TCGA-A7-A5ZX.A8 | E-DOC.pdf |

Surgical Pathology report

A. Lymph Nodes, left auxiliary sentinel, excision -
Metastatic carcinoma in two of two (2/2) lymph nodes in this part.

B. Breast, right, excision -
Invasive lobular carcinoma, 0.5 cm in greatest dimension (see microscopic description, including for prognostic marker results).
Lobular carcinoma-in-situ.
Fibrocystic changes, with microcalcifications present.
Skin, nipple, and deep margin negative for tumor.

C. Breast, left, excision

[Submit for review]

AUTOMATED QUALITY ASSURANCE TESTING OF STRUCTURED CLINICAL DATA

BACKGROUND OF THE DISCLOSURE

1. Field of the Invention

This application is directed to systems and methods for ensuring accurate data entry in one or more computer systems.

2. Description of the Related Art

In precision medicine, physicians and other clinicians provide medical care designed to optimize efficiency or therapeutic benefit for patients on the basis of their particular characteristics. Each patient is different, and their different needs and conditions can present a challenge to health systems that must grapple with providing the right resources to their clinicians, at the right time, for the right patients. Health systems have a significant need for systems and methods that allow for precision-level analysis of patient health needs, in order to provide the right resources, at the right time, to the right patients.

Rich and meaningful data can be found in source clinical documents and records, such as diagnosis, progress notes, pathology reports, radiology reports, lab test results, follow-up notes, images, and flow sheets. These types of records are referred to as "raw clinical data." However, many electronic health records do not include robust structured data fields that permit storage of clinical data in a structured format. Where electronic medical record systems capture clinical data in a structured format, they do so with a primary focus on data fields required for billing operations or compliance with regulatory requirements. The remainder of a patient's record remains isolated, unstructured and inaccessible within text-based or other raw documents, which may even be stored in adjacent systems outside of the formal electronic health record. Additionally, physicians and other clinicians would be overburdened by having to manually record hundreds of data elements across hundreds of discrete data fields.

As a result, most raw clinical data is not structured in the medical record. Hospital systems, therefore, are unable to mine and/or uncover many different types of clinical data in an automated, efficient process. This gap in data accessibility can limit a hospital system's ability to plan for precision medicine care, which in turn limits a clinician's ability to provide such care.

Several software applications have been developed to provide automated structuring, e.g., through natural language processing or other efforts to identify concepts or other medical ontological terms within the data. Like manual structuring, however, many of such efforts remain limited by errors or incomplete information.

Efforts to structure clinical data also may be limited by conflicting information within a single patient's record or among multiple records within an institution. For example, where health systems have structured their data, they may have done so in different formats. Different health systems may have one data structure for oncology data, a different data structure for genomic sequencing data, and yet another different data structure for radiology data. Additionally, different health systems may have different data structures for the same type of clinical data. For instance, one health system may use one EMR for its oncology data, while a second health system uses a different EMR for its oncology data. The data schema in each EMR will usually be different. Sometimes, a health system may even store the same type of data in different formats throughout its organization. Determination of data quality across various data sources is both a common occurrence and challenge within the healthcare industry.

What is needed is a system that addresses one or more of these challenges.

SUMMARY OF THE INVENTION

In one aspect, a system and method that provides automated quality assurance testing of structured clinical data derived from raw data or other, differently-structured data is disclosed. The system may analyze the clinical data on its own merits using one or more data validation checks or automated test suites in order to determine whether the structured version of the data satisfies a threshold for accuracy. The test suites may rely on an iterative or recursive methodology, in which previous analyses and their respective successes or failures may be used to support or modify the test suites.

Additionally or alternatively, the system may employ inter-rater reliability techniques, in which a plurality of users may evaluate identical portions of a data set to determine an accurate structured result for that data and/or to determine the accuracy of one or more of the user's attempts to structure the data.

BRIEF DESCRIPTION OF THE DRAWINGS

FIG. 1 shows an exemplary user interface that a clinical data analyst may utilize to structure clinical data from raw clinical data;

FIG. 2 depicts one example of EMR-extracted structured data that includes a payload of diagnosis-related data;

FIG. 3 depicts one example of EMR-extracted structured data that includes a payload of medication-related data;

FIG. 4 depicts a user interface that may be used by a conflict resolution user when a complex disagreement is identified for a patient record;

FIG. 5 depicts a user interface that may be used by a conflict resolution user when a more straightforward disagreement is identified for a patient record;

FIG. 9 depicts one example of a user interface through which a manager-level user can view and maintain validations, quickly determine which patient cases have passed or failed, obtain the specific detail about any failed validation, and quickly re-assign cases for further manual QA and issue resolution prior to clinical sign-out and approval;

FIG. 14 depicts another visualization of the exemplary user interface of FIG. 13;

Figure 16:
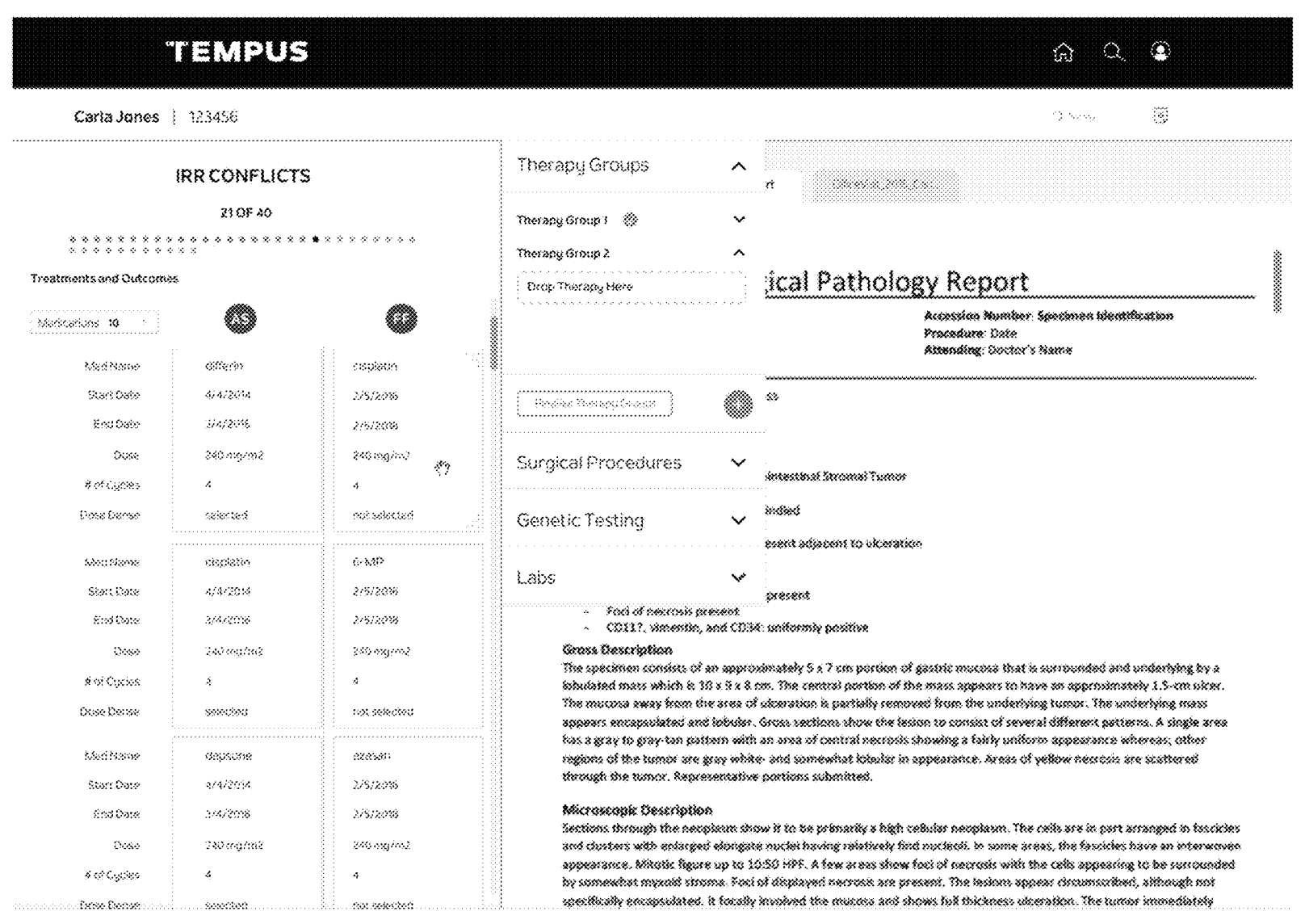

FIG. 16 depicts a second example of various metrics or reports generated by the present system;

DETAILED DESCRIPTION

Figure 7:
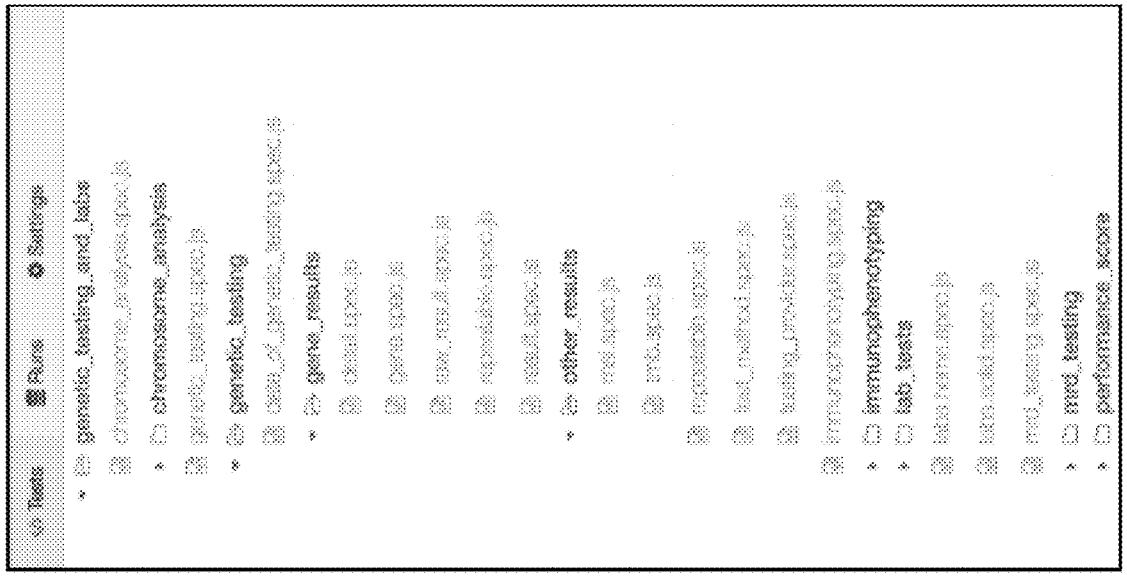
FIG. 7 depicts an exemplary test suite for determining sufficiency of a structured and/or abstracted instance of genetic testing.

A comprehensive data integrity evaluation and validation system is described herein, the system usable, e.g., to generate a definitive clinical record for a patient or consistency among groups, projects, or cohorts of patients. Due to the quantity and varying intricacy or elements of a clinical record, multiple categories of basic and complex validations may be needed to provide the requisite completeness and accuracy. In the functionality described below, various authors use software tools to compose validation rules that can be run independently on one or more patient records or applied in aggregate to all patient records comprising a given grouping, project or defined cohort.

These validations can be applied to a specific attribute (e.g. gender) or to a combination of attributes (e.g. gender and primary diagnosis) that results in the authoring of basic and advanced rule-based logic. In particular, the system may include a dynamic user interface enabling a user to design and build a new query by selecting one or more attributes represented in the system and then associating a desired rule (e.g. is present, is above/below/within a certain threshold value or range, etc.) with those attributes. Validation rules can operate in a stand-alone fashion or can be chained and/or linked together at a project and/or patient cohort level.

The construction of these validations is performed through the selection of one or more existing query sets as part of a validation query and/or through the design of a new query. Alternatively, validation checks can also be grouped and bundled into query sets or used individually as part of an ad-hoc quality assurance check initiated either manually or automatically upon delivery of a cohort of patient data. Still further, the system may maintain the ability to programmatically seed and/or populate a predefined set of validation rules that may be applicable to one or more streams.

A validation rule may be composed of a seeded set of rules and/or checks that enable data integrity. Examples of validation rules may include date-related rules such as including a date field and requiring an entry in that field, confirming whether a date is within a proper time period (e.g., providing an error if the rule requires the date to be earlier than or equal to the present date and the entered date is sometime in the future, or requiring a future date and the entered date is in the past), confirming that an entered value is within a predetermined range (e.g., an ECOG value must be between 0 and 5 or a Karnofsky score must be between 0 and 100), determining whether a metastatic site distance is sufficiently close to a tumor site diagnosis, or determining whether data received in a certain field conflicts with entered data in another field (e.g., any non-zero entry or any entry whatsoever in a gravidity field should return an error if the patient's gender in another field is indicated to be "male" or given a certain diagnosis or cancer sub-type, or an entered staging value is invalid given a cancer diagnosis or sub-type entry in another field).

From a system perspective, a series of API endpoints await a sufficiently articulated and valid rule definition as well as a corresponding validation rule name. The API for the service may enable the creation, update, and/or deletion of the validations; alternatively, the validations may be managed in an administrative user interface or directly via database queries.

A plurality of rules optionally may be grouped as a set, as compared to being evaluated independently. Thus, in a separate transaction, a rule can be associated with a query set (a combination of validation queries) and/or a specific cohort of patients where it can be run automatically to detect data inconsistencies and anomalies. Query sets may be groupings of validation rules and checks that are grouped as a result of similarity in the types of checks performed and/or the needs of a quality assurance ("QA") user wanting to identify the integrity of patient records via use of bulk and/or combined validation rules and checks. Conversely, an example of a patient cohort includes a sub-group of patients with a certain diagnosis sub-type (e.g., ovarian or lung within a cancer type) and/or a sub-subgroup of patients with a particular diagnosis stage or molecular mutation or variant within the sub-group. It will be understood that patient cohorts are not limited to oncological areas of medicine but may apply to groupings of patients in other disease areas as well, such as cardiovascular disease, atrial fibrillation, immunodeficiency diseases, etc. With regard to patient cohorts, rules can be evaluated on those cohorts to determine if a subset of patients satisfy validation requirements specific to the subset as compared to generic rules that may apply to all patients.

Applying a query set to a patient record or a portion thereof may result in the system verifying an accuracy of the data structuring within an acceptable system- or user-defined threshold level, in which case the structured data may be deemed accepted and the patient record may be amended to include that structured data. In another instance, the query set result may indicate the presence of one or more errors in the data structuring, requiring further review and/or modifications to the structured data, and the patient record then may be amended to include the modified structured data.

Structuring Data

In order to properly apply the validation rules, it may be necessary to standardize, normalize, or otherwise structure the input data. Thus, systems and methods are described herein that permit the automatic analysis of different types of structured clinical data. The structured clinical data may differ on the basis of the types of data elements within each list of structured clinical data, the organization of data elements within a structured clinical data schema, or in other ways.

Within the context of the present disclosure, the following terms may be understood to have the following meanings:

"Structured" clinical data refers to clinical data that has been ingested into a structured format governed by a data schema. As one simple example, structured clinical data may be patient name, diagnosis date, and a list of medications, arranged in a JSON format. It should be understood that there are many, more complicated types of structured clinical data, which may take different formats.

"Data schema" means a particular set of data attributes and relationships therein that comprise a set of structured data to be used for various purposes (e.g. internal analysis, integration with purpose-built applications, etc.).

"Data element" means a particular clinical and/or phenotypic data attribute. For instance, a comorbidity (e.g. acute myocardial infarction), adverse event (e.g. conjunctivitis), performance score (e.g. ECOG score of 3), etc.

"Data value" means the value of the data in a data element. For instance, in a "Diagnosis Date" data element, the data value may be "Oct. 10, 2016".

Certain systems and methods described herein permit a patient's structured clinical record to be automatically evaluated and scored in a consistent manner, while also simultaneously allowing for the determination of data integrity across various data sources. In particular, given that a patient may have disparate structured data residing in multiple applications and/or EMR databases within and across institutions, it may be a challenge to determine whether the structured data that exists within these sources is at a sufficient level of granularity and/or accuracy when analyzed independently and/or combined. Issues also may arise relating to clinical informatics—where a particular raw value may not have been correlated with a recognized medical ontology and/or vocabulary. Given this context, a structured clinical record may benefit from the use of validation rules and checks like those described herein. In particular, because the data is structured, it may be possible to determine whether the particular data in a field is in an appropriate format, is in an acceptable range, etc. For example, with regard to lab results and/or readings, while certain such results may be represented as numbers, structuring that data may permit it to be captured in a manner that can be validated automatically and/or used for aggregate population evaluation. As these validation checks can apply across phenotypic/clinical, molecular and other types of patient-specific information from various structured data sources, a system as described in this application can uniquely identify and support the resolution of gaps in a patient's record. Additionally, with validation rules & checks as well as a toolset as described in this application, structured and unstructured data across multiple data sources can automatically be analyzed to ensure a higher degree of patient data accuracy and fidelity. Thus, in some aspects, inter-rater reliability and a comprehensive clinical data validation system facilitate the identification and resolution of gaps in a patient's record when abstracted across multiple disparate streams.

Certain systems and methods may be utilized within an overall clinical data structuring platform. The platform may include a workflow tool and an administrative user interface for querying, reporting, and output tagging.

In one aspect, the system may support externally sourced data validations and/or edit checks corresponding to custom data science analysis workflows as well as data integrity enforcement for various purposes, such as for clinical trial management. In this context, "externally sourced" may refer to validation rules or checks authored by one or more external parties, e.g., health systems, clinical trial management services, etc., importable and ingestible into the present validation system, for use and integration with other rules and/or validation checks. "Externally sourced" also may refer to ingestion of other validations originated by other individuals or applications other than the present validation system while still internal to the entity employing the present system.

Additionally or alternatively, the system may compare multiple sets of structured clinical data for a single patient, select the most correct data element for each of the structured data elements, and return a new list of structured clinical data containing the most correct data element value for each data element. The new list reflects a single "source of truth" for a patient based on the raw clinical data for that patient.

Certain systems and methods may make use of various systematic validation checks at multiple stages in a process that commences with raw data input and ends with the data being curated, including at a data abstraction stage and/or a quality assurance stage. Additional stages in this timeline may include a data sufficiency score-carding stage in which the raw inputs are analyzed to determine whether they contain a sufficient amount of clinical data to proceed with the abstraction stage, and a downstream stage in which validation checks are used for patient cohorts. Thus, these systematic validation checks can be applied before data abstraction of raw clinical documents and notes. Additionally or alternatively, once the data abstraction process has been completed, the validation checks can be re-run or re-initiated to evaluate the quality of the abstraction.

In certain embodiments, the structured clinical data may be merged into a larger dataset. The larger dataset may have the same or a similar data schema to the structured clinical data. The larger dataset may be used for the conduct of research, may be associated with published research or clinical guidelines, and may be provided to third parties for their own research and analysis.

Figure 1:
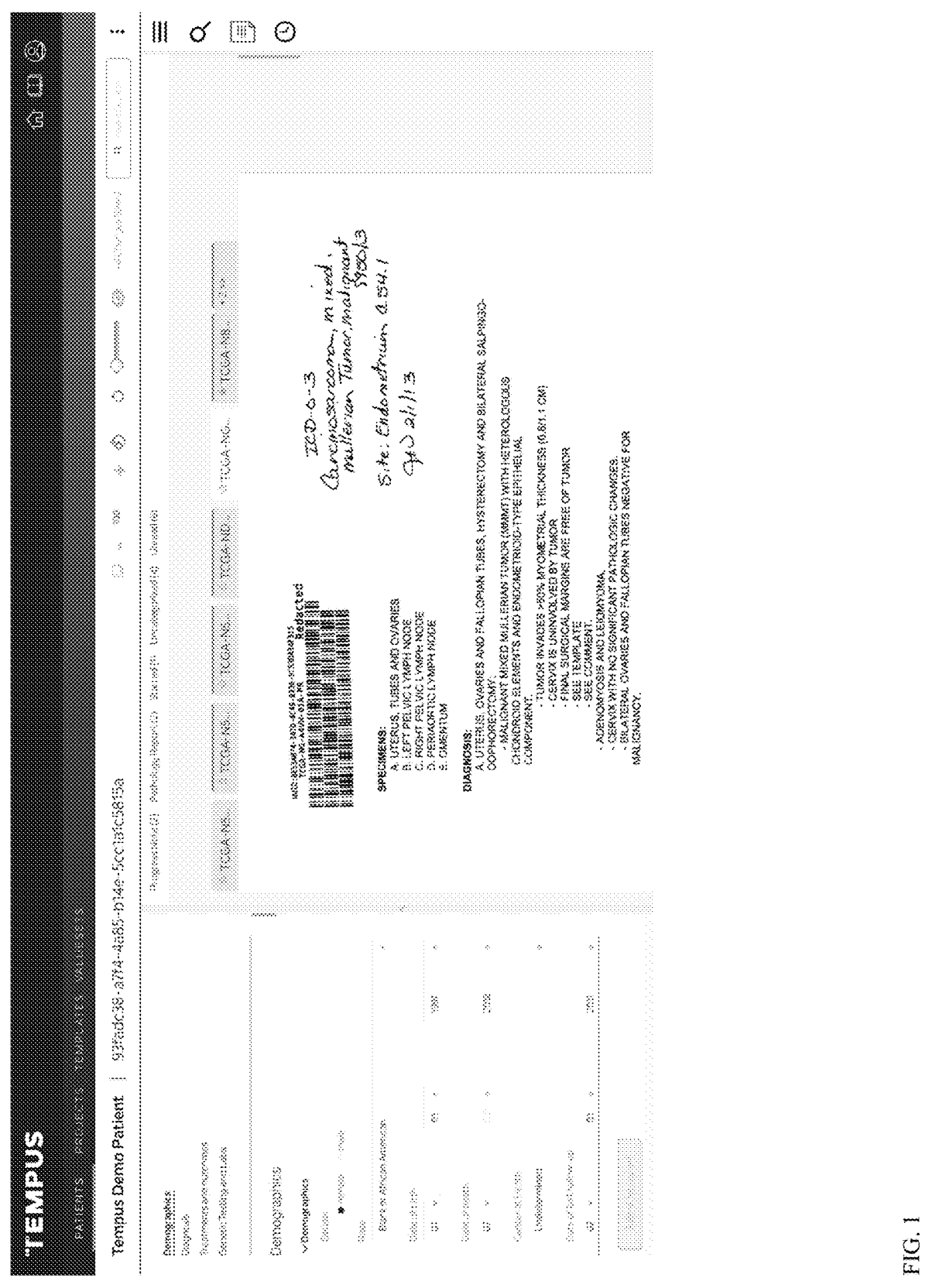

Turning now to FIG. 1, an exemplary user interface that a clinical data analyst may utilize to structure clinical data from raw clinical data is depicted.

In one aspect, the input data may be abstracted data that signifies a comprehensive, dynamic representation of a patient's clinical attributes across multiple categories, e.g., demographics, diagnosis, treatments, outcomes, genetic testing, labs, etc. Within each of these categories, attributes may be repeated to reflect multiple instances of a particular clinical data attribute present in multiple locations within the patient data. In particular, since abstraction is based on a full history of a patient's clinical record and associated documents, multiple attributes may be repeated across different data collection time periods and visit dates. For example, attributes like demographics (e.g. smoking status), treatments (e.g. therapies prescribed), outcomes (e.g. RECIST response level), and others can have one or more values ascribed to a given patient's abstracted clinical attributes.

In a second aspect, patient data can be extracted from source records, research projects, tracking sheets and the like. For example, sample source fields from unstructured flat files may include: enrollment_date, age_at_enrollment, sex, race, marital status, gravidity, menopause, cancer_status, age_at_diagnosis, laterality, T_stage_clinical, T_stage_pathological, histology, grade, etc., and the system may extract both the source fields as well as their respective data values.

In both aspects, the form of this input data often is inconsistent and dynamic to the principal investigator, researcher and/or partnering organization providing the patient data. For example, data models may vary substantially between a researcher, principal investigator and/or organization collecting and maintaining patient data. Additionally, since the data can be collected in real-time from various systems or data capture mechanisms, the raw data ascribed to the data model must be considered capable of dynamic, continuous updates as more information is obtained and/or recorded. As a result, a mapping exercise may be required to relate information from unstructured data originating in flat files into a canonical schema, format and/or model for evaluation purposes. Mapping also may be required to be able to run validation rules and checks across consistent data that has been merged into a single data model and/or schema for evaluation. In particular, the mapping exercise may identify source data fields and attributes from the data provider, e.g., a third party organization or researcher, and analyze that data in its raw form in order to determine linkages between the data and medical concepts or terminology reflected by the data and a data model used by the system. Such concept mapping may be performed manually by specially-trained informatics engineers or other specialists or one or more software applications specifically designed to undertake such mapping, as would be appreciated by one of ordinary skill in the relevant art.

In a third aspect, patient data may be Electronic Medical Record (EMR)-extracted structured data. This data can include a set of text strings representing various clinical attributes but may also include various ontological code systems and concepts to represent each text string in a way that can be compared against other data sets and/or validations. As a result of this structuring, the data mapping exercise may be significantly more straightforward than the exercise required for either of the other two instances. FIG. 2 depicts one example of EMR-extracted structured data that includes a payload of diagnosis-related data, specifically, data pertaining to a diagnosis of Malignant neoplasm of larynx, unspecified. Similarly, FIG. 3 depicts one example of EMR-extracted structured data relating to the medication Paclitaxel, provided intravenously.

In a fourth aspect, patient data may be extracted through a clinical concept identification, extraction, prediction, and learning engine such as the one described in the commonly-owned U.S. Pat. No. 10,395,772, titled "Mobile Supplementation, Extraction, and Analysis of Health Records," and issued Aug. 27, 2019, the contents of which are incorporated herein by reference in their entirety. Additional relevant details may be found in the commonly-owned U.S. patent application Ser. No. 16/702,510, titled "Clinical Concept Identification, Extraction, and Prediction System and Related Methods," filed Dec. 3, 2019, the contents of which also are incorporated herein by reference in their entirety. The output of this engine may be a configurable and extensible set of predictions about a given patient's clinical attributes across a variety of content types. These types may include (but may not be limited to) primary diagnosis & metastases sites, tumor characterization histology, standard grade, tumor characterization alternative grade, medication/ingredient, associated outcomes, procedures, adverse events, comorbidities, smoking status, performance scores, radiotherapies, imaging modality, etc.

Triggering Analysis Once Data is Structured

In order to make use of data from one or more of these streams, the system may be configured to automatically initiate the evaluation of both partial and fully structured patient clinical records across multiple sources and/or streams through a variety of triggering events. Such events may include, e.g.: (1) receiving an on-demand request, e.g., via a job runner by an Administrative user using an Administrator-driven user interface that can initiate the process programmatically, (2) via a background service triggered upon receipt of new software code commits or corresponding application build phases, (3) when new data is either received or ingested across sources and streams, (4) upon achieving a sufficient inter-rater or intra-rater reliability scoring system, which is run automatically on a configurable percentage of patient records as part of a project or batch, (5) upon completion of either a case abstraction and/or QA activity, (6) a bulk initiation of evaluation of multiple structured clinical records once all have been completed, e.g., upon receipt of clinical data and/or records for patients participating in an institution's clinical trial, which may be obtained via a site coordinator, via EMR or source records, or (7) real-time analysis during creation of a patient note or other clinical data. Each of these trigger events is discussed in greater detail, as follows. Data analysis also may be triggered in one or more other ways, including via an automated trigger. Such automated triggers may occur, e.g., when a case has been submitted and recorded successfully, when a case has generated a data product representing all of the structured content, or in preparation for data delivery to a partner expecting a set of de-identified patient records containing structured clinical records that have been validated for quality, accuracy and consistency.

Trigger #1 (on-demand): a user with appropriate authorization can manually initiate one or more distinct tests to support the evaluation of one or more patient clinical records. In its default state, this functionality manifests itself as part of a graphical user interface presented after entering in a specific request for one or more tests at a terminal window command line.

Trigger #2 (on receipt of code commits): tests can be initiated en masse via a background service or selectively when only a subset of tests are required to validate specific patient clinical data and/or attributes. In this aspect, validation may take advantage of "continuous integration," or the practice of integrating new code with existing code while embedding automated testing and checks into this process to minimize and/or eliminate gaps and issues in production-level software and applications. As part of this process, new code commits are made, reviewed, approved and merged into various code branches for subsequent application build phases while intermediate software (e.g. Jenkins) maintains responsibility for running one or more test suites programmatically and recording their output (e.g. failed, pending and passed) as well as collecting details, stacktraces and/or screenshots resulting from these tests.

Trigger #3 (new data ingested): an integration engine and/or intermediate data lake receives and processes new structured data which may also initiate corresponding tests to evaluate and score the data as its own distinct stream as well as comparatively to any existing data received for the patient. In one possible implementation, an integration engine may receive a stream of XML and/or JSON content comprising structured data and corresponding ontological code systems and concepts as extracted from a health system's EMR at a single point in time. Upon receipt, this data would be evaluated against one or more test suites for accuracy, coverage and/or insufficiency. It may also be compared and evaluated relative to other patient record data received via other sources and similarly run through one or more test suites. In another possible implementation, the system may receive a FHIR-compliant payload from partners that contains one or more genetic/genomic testing results for one or more patients. In this example, the test suite for genetic testing referenced above may be run programmatically to evaluate the integrity of this data and may also be compared and evaluated relative to other genetic testing content already ingested and/or abstracted as part of one or more patient records.

Trigger #4A (inter-rater reliability): the system will evaluate two instances of a patient's abstracted clinical data and compose a score at both the case and field-levels to determine a level of agreement between a plurality of abstractors (or "raters") in order to determine whether to automatically begin the evaluation process. In this example, "automatically" may refer to a systematic assignment of a subset of patient cases that will be abstracted by two distinct individuals in a "double-blind" manner where the reviewer may also be unaware of participant identities. Further, a scoring scheme is used to calculate the proficiency and accuracy of each submission by taking into account the modifications and updates made by a conflict resolution user.

The system may assign a first version or instance of a case or data stream to a first rater and a second version or instance of the case or data stream to a second rater, i.e., the plurality of raters may review the same subset of cases or records, after which the system may determine whether there is a sufficiently high degree of overlap and/or agreement between each rater's abstraction. When the requisite threshold is not met, a third-party conflict resolver may review the raw clinical data and each rater's abstraction content in order to generate a de facto or "best" abstraction of the patient record. In one aspect, the conflict resolver may select from among the abstractions provided by the other raters. In another aspect, the conflict resolver additionally or alternatively may provide its own abstraction and select the "best" abstraction from the group that includes its own abstraction and those of the other raters.

Figure 4:
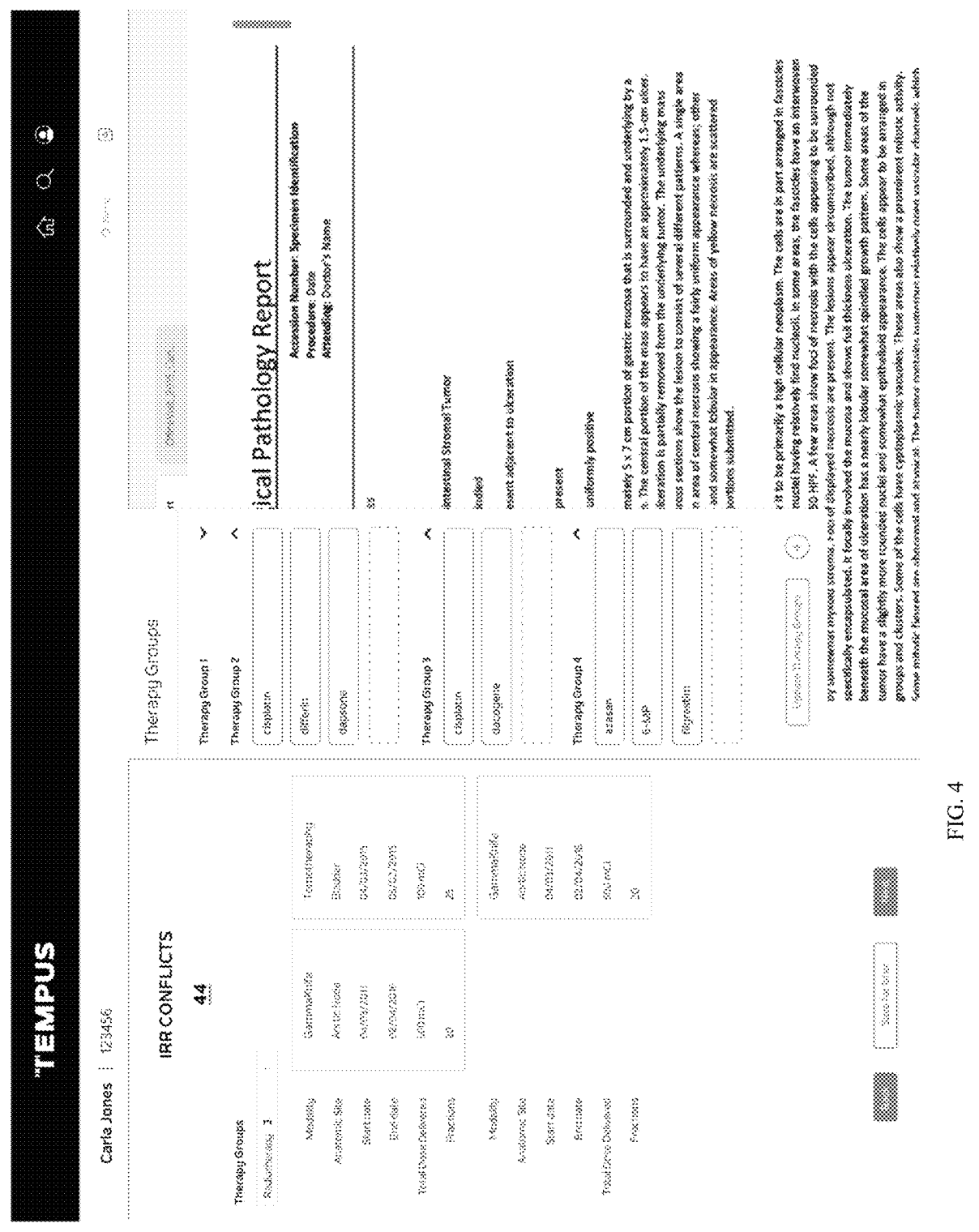

With regard to this trigger, FIG. 4 illustrates one of the steps to be performed by a conflict resolution user when a complex disagreement is identified for a patient record. In this example, a conflict resolver must evaluate the radiotherapies cited by the two abstractors and determine which are in fact appropriate for the "de facto" patient clinical record by moving the most correct items to therapy groups.

Figure 5:
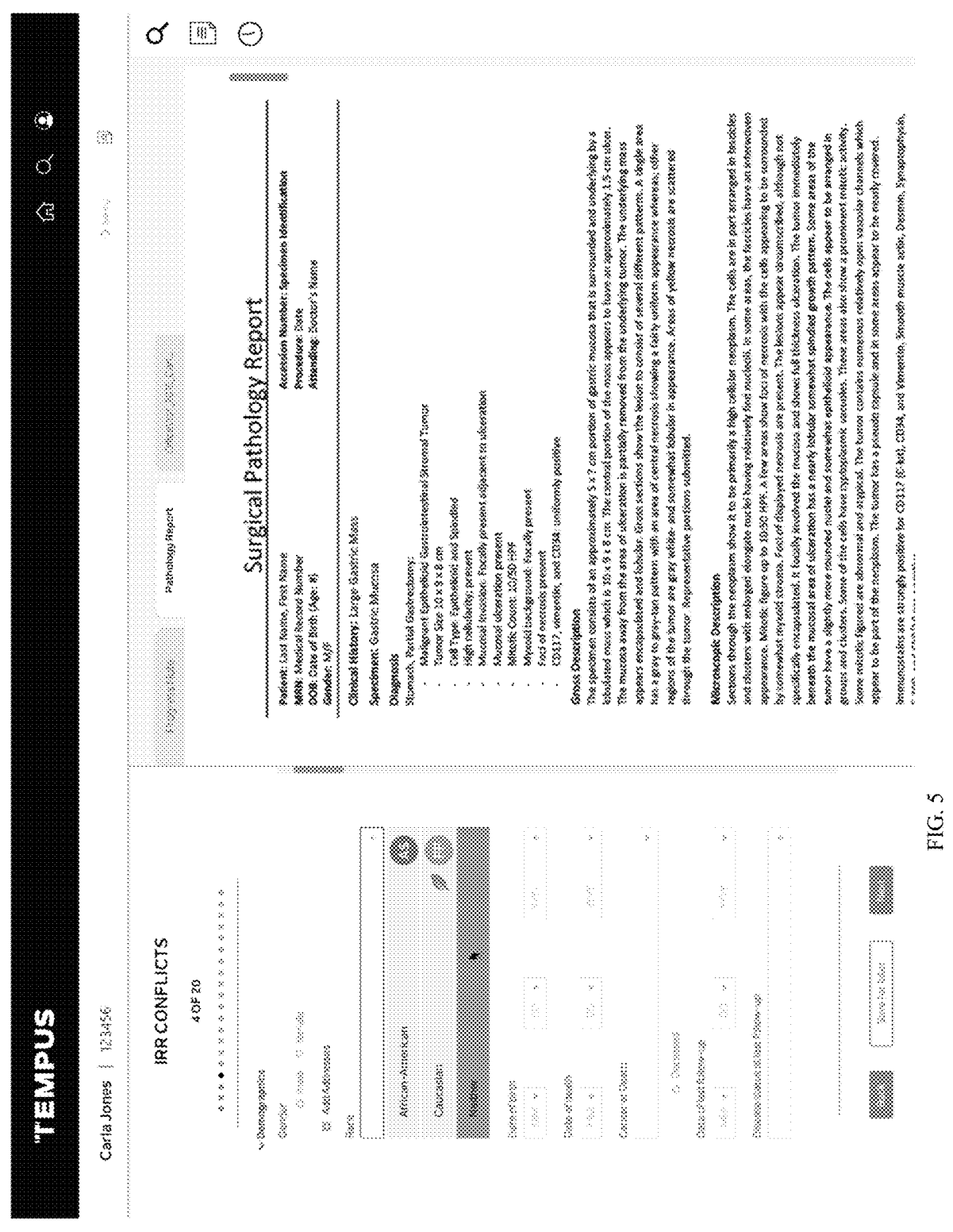

Conversely, FIG. 5 illustrates one of the steps to be performed by a conflict resolution user when a basic disagreement is identified for a patient record. In this example, a conflict resolver must evaluate the demographic data cited by the two abstractors and determine which are in fact appropriate for the "de facto" patient clinical record by selecting the correct "race" clinical data value.

Trigger #4B (intra-rater reliability): like the previously-disclosed trigger, the system also may be used to evaluate a plurality of abstractions from a single rater, in order to determine how consistent the rater is in his or her efforts. The notes or other clinical data reviewed by the rater may relate to the same patient, e.g., different portions of a patient's record, or they may be similar or distinct portions of raw clinical data from multiple patients.

Trigger #5 (case abstraction completion and/or quality assurance completion): clinical data attributes for the patient record may be evaluated systematically for gaps in logic through the use of a clinical data validation service that centralizes a number of rules (see below for details) and works in conjunction with a cohort sign-out process.

Trigger #6 (upon receipt of clinical data and/or records for patients participating in an institution's clinical trial): clinical data attributes for a patient potentially eligible for participation in a clinical trial may be evaluated on-demand or as part of a broader batch of patients from that institution on a rolling basis. With regard to this workflow, the present system and method may support the workflow's ability to identify gaps in clinical attributes that may be required for inclusion/exclusion criteria evaluation and matching.

Trigger #7 (on-demand analysis): structured data may be extracted, either directly or via a mapping procedure, from a clinical note while that note is being created or dictated by a physician or other clinician. The structured data is analyzed, and errors, incomplete information, or conflicting information in the underlying data are reported back to the clinician in real time.

Analysis Following Triggering Event

Figure 6:
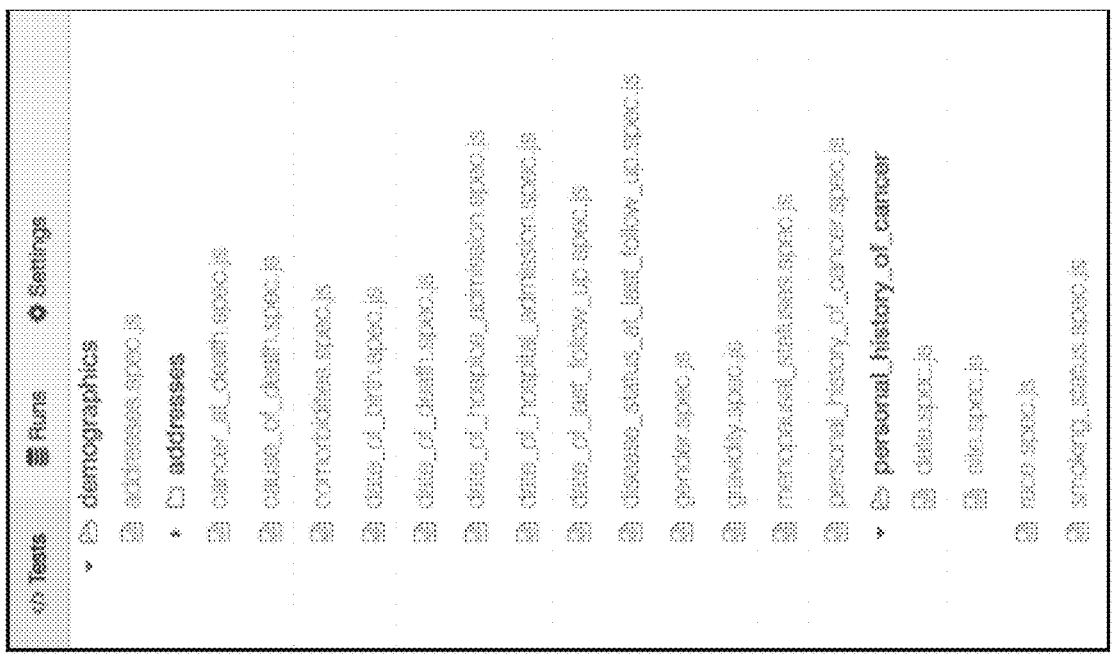
FIG. 6 depicts a list of test suites within a "demographics" root level category.

Regardless of the choice of triggering event, the default set of evaluation criteria (e.g. test suites) may be composed at a category-level (e.g. demographics, diagnosis, genetic testing and labs, treatments and outcomes) along with nested sub-groupings that allow for granular and precise evaluation of clinical patient attributes by type. For example, and with regard to the depiction in FIG. 6 of a list of test suites within a "demographics" root level category, a test may be written to determine whether a record of ovarian cancer was a correctly structured instance:

Primary tumor instance identified as part of a patient record

Tissue of origin identified for a corresponding primary tumor instance
 e.g. Ovary Date of diagnosis identified for a primary diagnosis
 e.g. Dec. 15, 2015

Date of recurrence identified for a primary diagnosis
 e.g. Mar. 5, 2016

Diagnosis (e.g. histology) identified for the corresponding primary diagnosis
 e.g. Ovarian stromal tumor Standard grade identified for the corresponding primary diagnosis
 e.g. Grade 2 (moderately differentiated)

AJCC staging identified for the corresponding primary diagnosis
 e.g. T1B, N0, M0 (Stage 1B)

In this example, a determination that the record was structured "correctly" may mean more than simply determining whether there are data values in each of the specified fields and attributes. Instead, correct structuring also may signify that all of the attributes listed were adequately provided and mapped to accepted and/or preferred medical concepts, i.e., that the requisite data was provided, represented, and properly fulfilled all validation checks managed by the system. Mapping may relate to both a system-defined data model as well as one or more external models, such as the Fast Healthcare Interoperability Resources ("FHIR") specification. In this regard, the system may include one or more test suites that define the criteria for the relevant categories and nested sub-groupings and then may execute relevant validation checks to carry out those test suites.

Medical concepts can span numerous dictionaries, vocabularies and ontologies, and data elements within structured data generally conform to a specific system, concept code and preferred text descriptor. For instance, in the example discussed above, for "Ovary," i.e., the tissue of origin identified for a corresponding primary tumor instance, the system may determine whether that data instance is mapped to the "SNOMED" code of 93934004 with a preferred text descriptor of "Primary malignant neoplasm of ovary (disorder)" in order to comply with a test suite that includes the same relationship.

In a second example, and with regard to FIG. 7, the test suite for determining sufficiency of a structured and/or abstracted instance of genetic testing may include evaluating whether values for the following criteria are present and accurately structured:

Initial genetic testing instance identified and/or added to a patient record

Date identified for an instance of genetic testing
 e.g. Jan. 1, 2017

Figure 8:
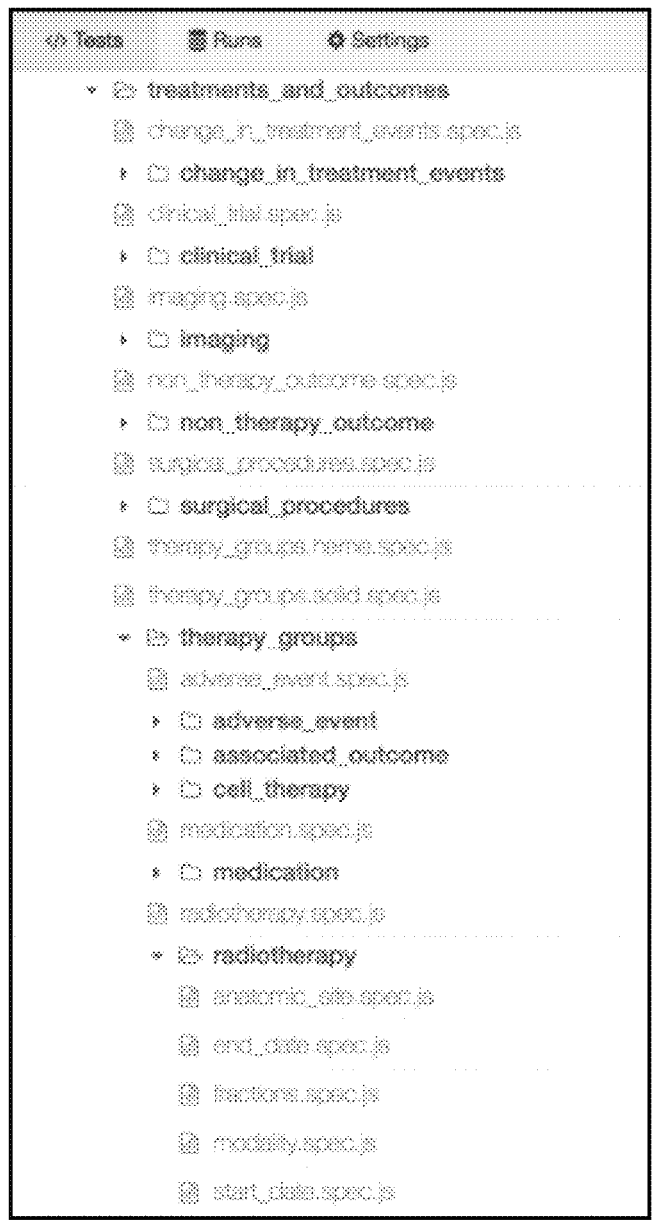
FIG. 8 depicts a second exemplary test suite for determining sufficiency of a structured and/or abstracted instance of genetic testing.

Testing provider identified for an instance of genetic testing
e.g. Tempus
Test method identified for an instance of genetic testing
e.g. Mutation analysis
Gene result detail identified for an instance of genetic testing
e.g. Gene: KRAS
e.g. Result: Amplification
e.g. Raw Result: 100
e.g. Detail: N/A
Tumor mutational burden identified for an instance of genetic testing
e.g. 10
Microsatellite instability identified for an instance of genetic testing
e.g. High In a third example, and with regard to FIG. 8, a test suite for determining sufficiency of a structured and/or abstracted instance of genetic testing may include the following criteria:

Initial genetic testing instance identified and/or added to a patient record
Date identified for an instance of genetic testing
e.g. Jan. 1, 2017
Testing provider identified for an instance of genetic testing
e.g. Tempus
Test method identified for an instance of genetic testing
e.g. Mutation analysis
Gene result detail identified for an instance of genetic testing
e.g. Gene: KRAS
e.g. Result: Amplification
e.g. Raw Result: 100
e.g. Detail: N/A
Tumor mutational burden identified for an instance of genetic testing
e.g. 10
Microsatellite instability identified for an instance of genetic testing
e.g. High In one aspect, the evaluation and/or analysis performed as part of the system referenced above may comprise a combination of several of the trigger mechanisms discussed above. Thus, the analysis of data can be initiated programmatically or manually by one or more of the triggers on a particular set of patient data records (either structured or unstructured) and from multiple disparate data sources. For example, the system may include: (1) automated and continuously maintained test suites specific to one or more clinical attributes and/or content types, (2) clinical data validation processes performed at run-time during abstraction as well as quality assurance activities, and (3) inter-rater reliability (IRR). Additionally, the triggers may evolve or be revised over time to generate a more robust, more complete quality assurance system. For example, test suites may grow continuously to support more templates or later-generated abstraction fields for clinical data structuring. Similarly, the clinical data validations (errors, warnings, etc.) may be maintained in a library programmatically via web service endpoints or a user interface that supports the addition of new validations and corresponding definitions of rules, e.g., using a rule builder. The system may generate multiple streams of abstracted clinical data that can be evaluated and re-assigned to a more sophisticated user with deeper clinical background to help resolve any conflicts, thereby producing a de facto "source of truth" for a given patient's clinical record.

In still another example, the system may rely on data from other patients to determine whether the data in a target patient's record appears correct or whether it may warrant an alert signifying a potential error or an otherwise unexpected finding. For each validation rule and/or check performed (or triggered) on a given patient record, anomalies can automatically be detected or ascertained when a newly validated patient record contains data (e.g. clinical or molecular) that have not been found in any previous patient records run through the validation rule and/or check. For example, a patient record may include both clinical and molecular data, where the molecular data may include data reflecting a "new" gene, in that there may not be much, if any, clinical knowledge regarding the medical effects of having the gene. In another example, a molecular variant present in structured data for a patient from a 3rd party NGS lab that is invalid or unknown to science may be flagged for manual review as it may have been mis-keyed or entered incorrectly into a structured clinical record. In both cases, the system may search its data store for indications of other patients with that gene. For example, the system may use a library of known valid molecular variants as well as a review of all previous molecular variants found in previous data structuring activities for other patient records to detect anomalous data elements. The system then may search for similarities in clinical data among those other patients in order to develop a template test suite. Thus, the system may assume that the other patients' clinical data is accurate, such that deviations from that data when a validation check is performed on a subject patient's data may trigger an alert to the provider or reviewer as to either an error in the subject patient's data or, alternatively, to an unexpected result that may warrant further investigation.

In one instance, validations may be fairly straightforward, e.g., when comparing different portions of a patient record, is the system able to extract a patient's gender from more than one location and do those gender-based attributes match up? In those instances, a test suite that instructs the system to query one or more known portions of a record for gender-identifying information, to review that information for internal consistency (if more than one portion of the record is considered), and to return that gender as an attribute for the patient may be usable for multiple use cases as a fairly generic test suite. In another example, the test suite may seek to compare the structured patient data against a set of one or more guidelines, e.g., clinical trial inputs or metrics reflecting general patient population results (e.g., survival, progression, etc.), to determine whether the patient's data is in-line with those guidelines or reflects a potential error or outlier.

In another instance, the validation may be structured to match a clinical practice guideline that must be met before a patient is eligible to receive a therapy. One example set of clinical practice guidelines is the National Comprehensive Cancer Network Clinical Practice Guidelines. A validation may be structured to include the relevant criteria from one or more practice guidelines. If the patient record contains information that permits the validation to pass successfully, then the patient may be permitted to receive the therapy.

In another instance, validations may be specific to certain use cases based, e.g., on other data extracted from a patient record. For example, certain types of cancer are gender-specific. Thus, a quality assurance validation or rule that says "if structured data extracted from the patient record includes an attribute for prostate cancer, then a patient gender of 'female' represents an error" is useful for prostate cancer use cases but not for other cancers or diseases.

In still another instance, validations may be multi-variable or require more than a simple cross-check of two fields against one another. For example, with regard to lung or breast cancer, a patient record may document scenarios that reflect valid or invalid staging, and the relevant cancer also may have subtypes that vary based on staging. Thus, a complete validation check of a test suite may require that the system evaluate all of the possibilities at each stage to determine whether the structured data is complete and internally consistent.

Still further, the system may include an automated process for evaluating each test suite to determine whether it represents an accurate test. That process may require running through each of the possibilities that are queried in the test suite and determining that none of the tests conflict with other tests in the suite. Thus, e.g., the system may assume that a first test yields a "true" or valid result. Then, given that result, the system determines whether it is possible for a second test to also yield a "true" or valid result. The system continues in that process until a "false" or invalid result is reached or until all tests have been evaluated. In the latter case, the system may recognize that the test suite does not include any failures and may publish the test suite for actual implementation. In the former case, once an invalid result is determined, the system may flag the test suite for further review and either amendment or definitive approval, despite the invalid result.

One objective of the system is to allow for the creation, management and assignment of specific clinical data fields and their corresponding attributes via a single user interface. A dynamic management and rendering engine for template-specific fields enables the system to achieve this objective by permitting different classes of users to rapidly configure new templates with custom field configurations in minutes without code by employing a user interface that permits those users to select both the fields, as well as the hierarchy among the fields, that are desired for a given clinical data structuring project or use case. Templates may drive a determination of what content from the raw data is available to an abstractor. Finally, the system maintains a version history of every template modification made by authorized users for auditing purposes.

In addition to the single-user-centric analysis described above, in another aspect, validations can be leveraged at a more granular project-specific level (rather than at an individual level or a cohort level), which may allow for the evaluation and scoring of specific template configurations as well as their corresponding data fields. Thus, rather than running validations against a single patient's clinical data elements and content generally, the validation service also may be run with a batch or bulk set of patient clinical data elements that correspond to one or more projects. Data may be sourced from one or more sources, including upstream abstracted patient content (e.g., prior to structuring) or from more finalized versions of the data (e.g., from a downstream data warehouse in a structured format). Like the single-user-centric analysis described above, these bulk or test validation service checks may be configured to run either sequentially or simultaneously. The system may be configured to perform these validation checks on patients associated with projects that have been configured to these templates to ensure that data has been abstracted, captured and/or encoded properly.

Results of the foregoing validations may be output as structured code, e.g., in a JSON file format. The file may include one or more indicators describing which clinical data attributes passed or failed a particular validation. Similarly, results of a test suite processing all clinical data attributes may produce a result output as structured code, e.g., also in a JSON format, that describes which particular test(s) within the suite passed or failed for one or more given patient records passed to it.

Various System-Supported User Roles or Use Cases

The system may be usable by a plurality of different users having distinct roles. For example, the following list describes various user roles or use cases, the corresponding actions each user may take, and one or more benefits that may result from use of the system as a result of those actions:

A clinical manager may want to evaluate a single patient, a project, an in-progress or completed cohort or one or more patients abstracted and/or QA'ed by a specific abstractor or lead user for accuracy. Additionally, this user may want to obtain an analysis of a data stream sourced externally (e.g. via EMR or structured data extract) to determine the need for further incremental abstraction of a patient's clinical record.

A single abstracted patient can be evaluated for accuracy through the use of the clinical data validation service either upon request, when the corresponding patient case is being submitted via Workbench or when clinical attributes are modified. Validation rules are run atop all structured clinical data for a single abstracted patient and pass/fail assignments are made as a result. The clinical data validation service also maintains an "effective as of" timestamp that ensures that only appropriate validations are run on a single abstracted patient at that point in time.

A project can be evaluated for accuracy through the use of the clinical data validation service either upon request or when the project is used as a filter within the QA Manager Console user interface. At this point in time, validation rules will have already been run atop all structured clinical data for all completed and submitted patients within the given project and pass/fail assignments are retrieved as a result. The clinical data validation service also maintains an "effective as of" timestamp that ensures that only appropriate validations are run on abstracted patients within a project at that point in time.

A cohort can similarly be evaluated for accuracy through the use of the clinical data validation service either upon request or when the cohort is used as a filter within the QA Manager Console. At this point in time, validation rules will have already been run atop all structured clinical data for all completed and submitted patients with the given cohort and pass/fail assignments are retrieved as a result. The clinical data validation service also maintains an "effective as of" timestamp that ensures that only appropriate validations are run on abstracted patients within a cohort at that point in time.

Externally sourced data streams may first be ingested and mapped to a source-specific schema by a member of an integrations team. Subsequently, the schema may be aligned to a clinical data model by a member of an informatics team that allows for mapping of concepts to a canonical set of systems, codes, and values. After the schema mapping and concept mapping steps, the clinical data validation service can evaluate an externally sourced patient record upon request by using the default set of validations checks. Further, source-specific custom rules and validations may be authored within the QA Manager Console to ensure proper coverage of all desired data integrity checks.

A clinical abstraction lead may want to identify gaps in abstraction for a patient and/or project assigned to their abstraction team, perhaps specific to a cancer type (e.g. colorectal team). In this instance, the clinical abstraction lead may want to obtain the IRR score for a project, manually initiate a test suite for one or more clinical data attributes as well as perform various validation checks. IRR scores at a project-level are aggregated and averaged across all eligible and completed IRR cases within that project. As a reminder, IRR case agreement thresholds and case eligibility percentage are configurable at the project level and will vary. A global set of validation checks are available via the clinical data validation service and can be run atop one or more patient records corresponding to a project.

A clinical data abstractor may want to preview content ingested from third party sources into various data streams and obtain a report including quantitative insights specific to clinical data attributes (e.g. medications, procedures, adverse events, genetic testing, etc) that will help them to more fully abstract a patient's clinical record from various disparate sources.

An operational lead may want to better understand data coverage and quality gaps specific to one or more patients or in aggregate across specific projects/cohorts. Further, they may want to receive automated notifications and warnings that will alert them to take action directly with health system content partners when data validations fail and/or the automated evaluation and scoring for various clinical data streams is insufficient.

A data scientist may want to integrate with the system to better train machine learning models based on various levels of priority and/or a trust scale for various clinical data ingested and/or structured across clinical data streams. For example, a project or cohort with a high IRR score, near-perfect clinical data validation checks and automated test suites passing may be treated preferentially to other unstructured or semi-structured clinical data with lower scores.

An integration and/or infrastructure engineer may want to monitor various clinical data streams being ingested from external sources to verify connectivity, data sufficiency as well as quality over time.

A quality assurance engineer may want to compare the output of their manually maintained clinical data test suites against externally sourced content programmatically or on an ad-hoc basis.

A product manager may want to better understand the project, cohort and/or field level scoring of either/both abstracted and structured data to determine further improvements to various workflows, user interfaces and design patterns to accelerate and further streamline the data structuring operation.

For each of the triggers discussed above, as well as for other events that may trigger the quality assurance testing disclosed herein, the system maintains a continuously growing set of stream-specific validations, warnings, and errors that help proactively inform and/or alert administrators of patient data quality and integrity issues. By making a request to the clinical data validation service, a supported application and any of its users can quickly identify whether a patient case, either individually or one within a specific cohort, has passed or failed one or more validation checks.

Validations may be managed through a QA Manager Console user interface where they are constructed and/or grouped for use as part of quality assurance activities (at a batch and/or cohort level) and as part of on-demand evaluation criteria for one or more patient records. These validations are also useful when accounting for inclusion and exclusion criteria specific to patient cohorts for research and/or clinical trial consideration purposes.

Figure 10:
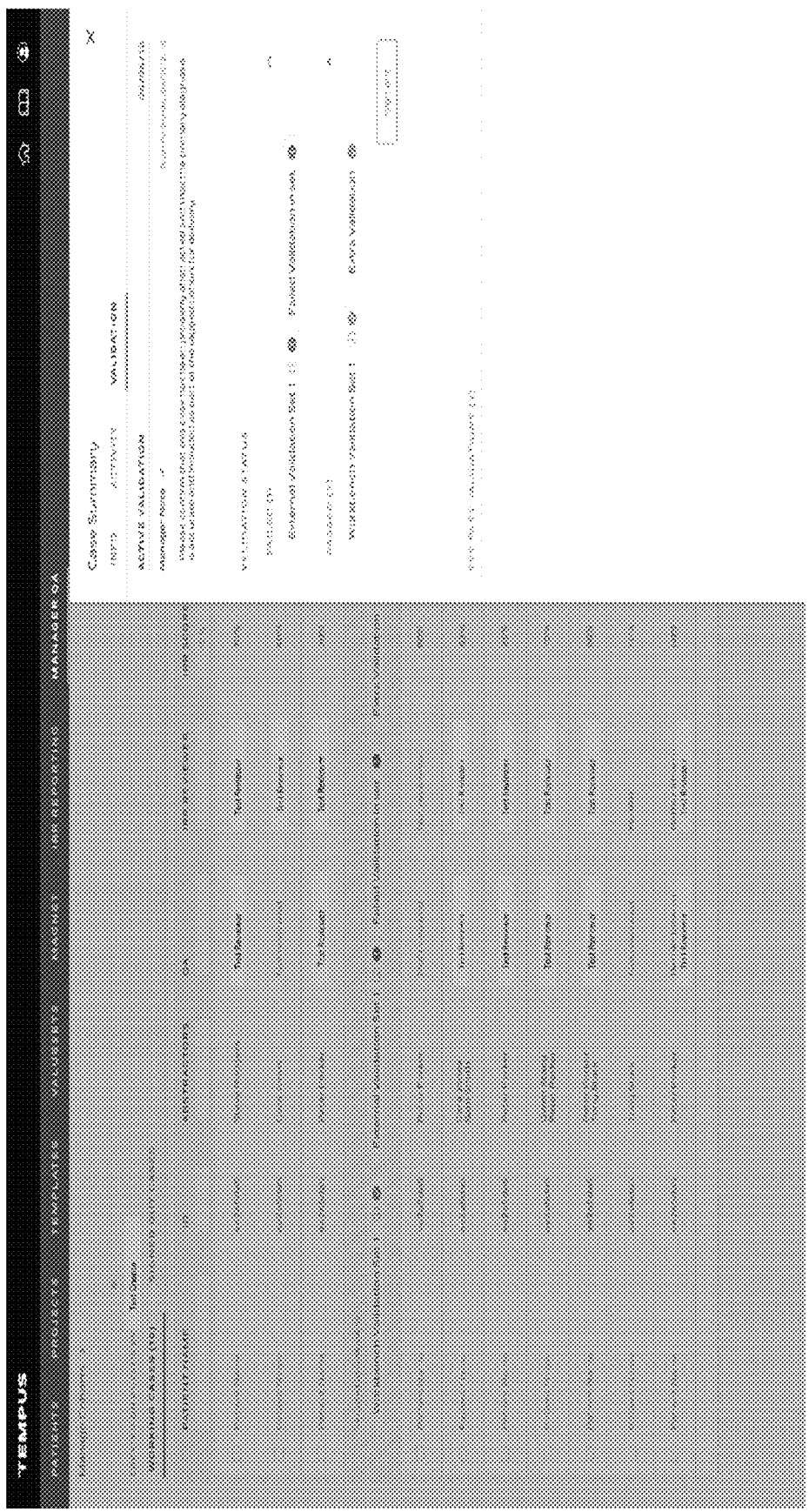
FIG. 10 depicts an exemplary user interface for performing quality assurance testing based on generic abstractions from raw documents.
Figure 11:
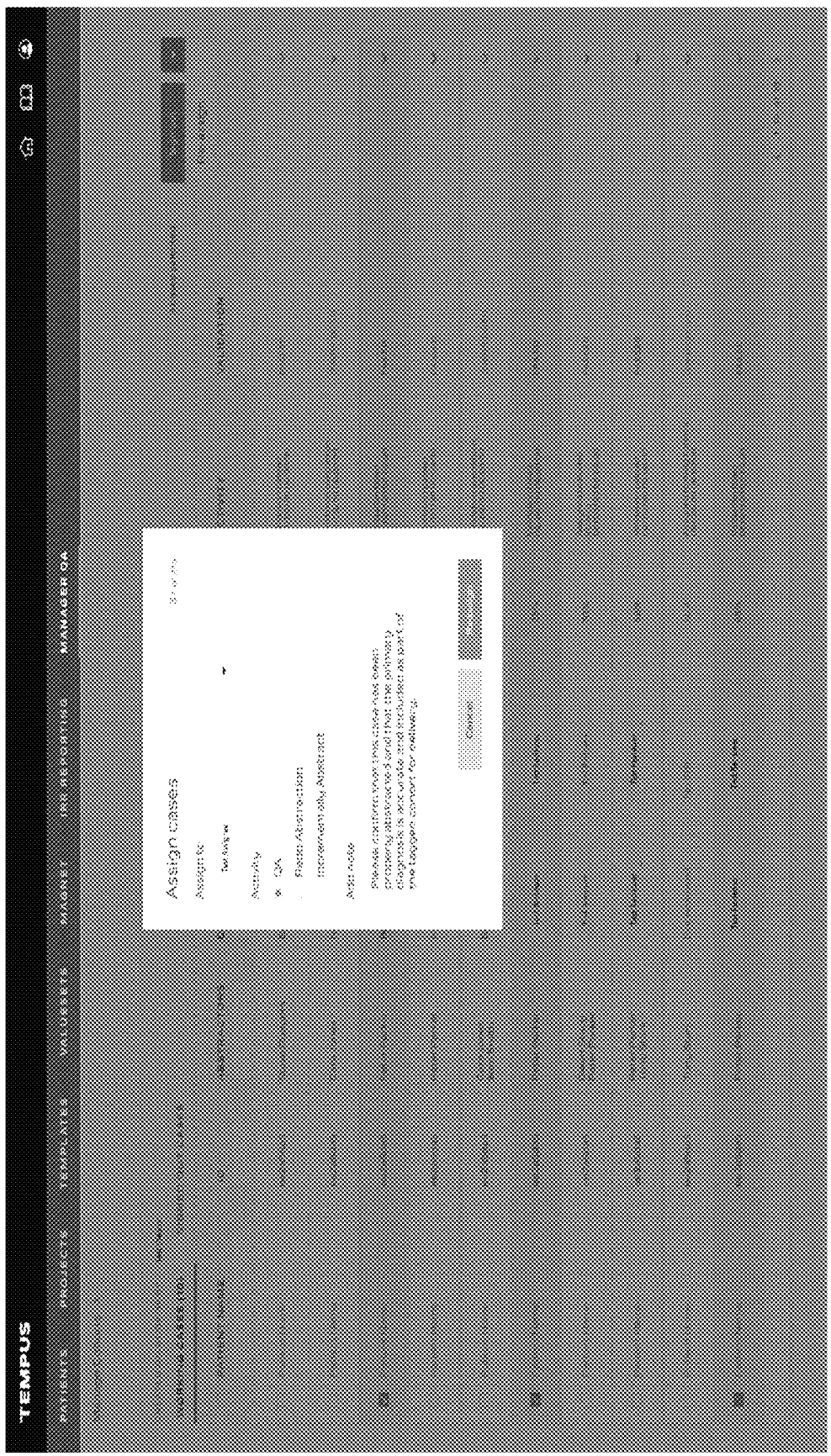
FIG. 11 depicts an exemplary user interface that is used to provide abstraction across multiple streams of raw clinical data and documents.
Figure 12:
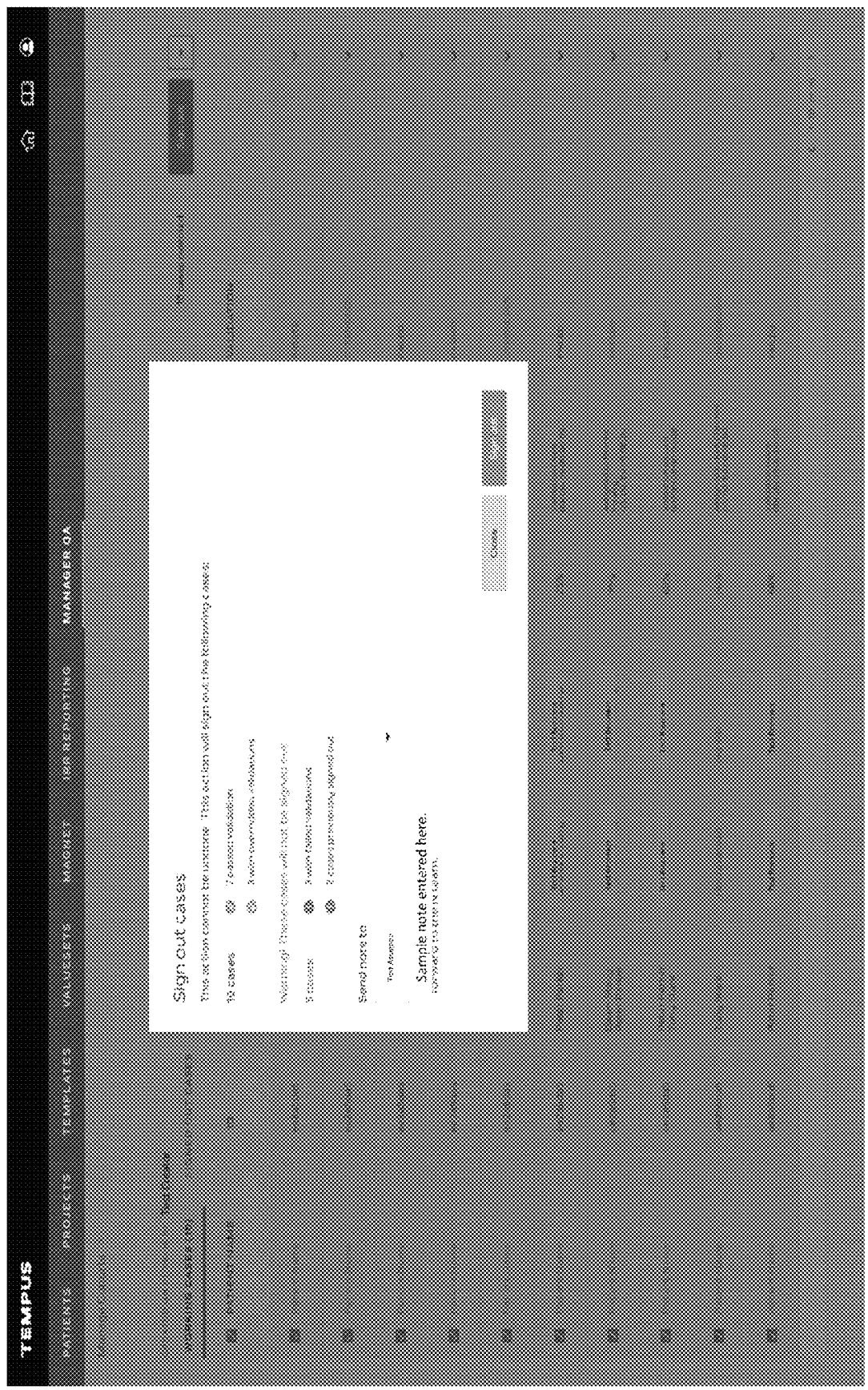
FIG. 12 depicts an exemplary user interface for performing an inter-rater reliability analysis.

FIGS. 9-12 depict one example of the user interface through which a manager-level user can view and maintain these validations, quickly determine which patient cases have passed or failed, obtain the specific detail about any failed validation, and quickly re-assign cases for further manual QA and issue resolution prior to clinical sign-out and approval. In particular, FIG. 10 depicts an exemplary user interface for performing quality assurance testing based on generic abstractions from raw documents. FIG. 11 depicts an exemplary user interface that is used to provide abstraction across multiple streams of raw clinical data and documents. FIG. 12 depicts an exemplary user interface for performing an inter-rater reliability analysis.

Figure 13:
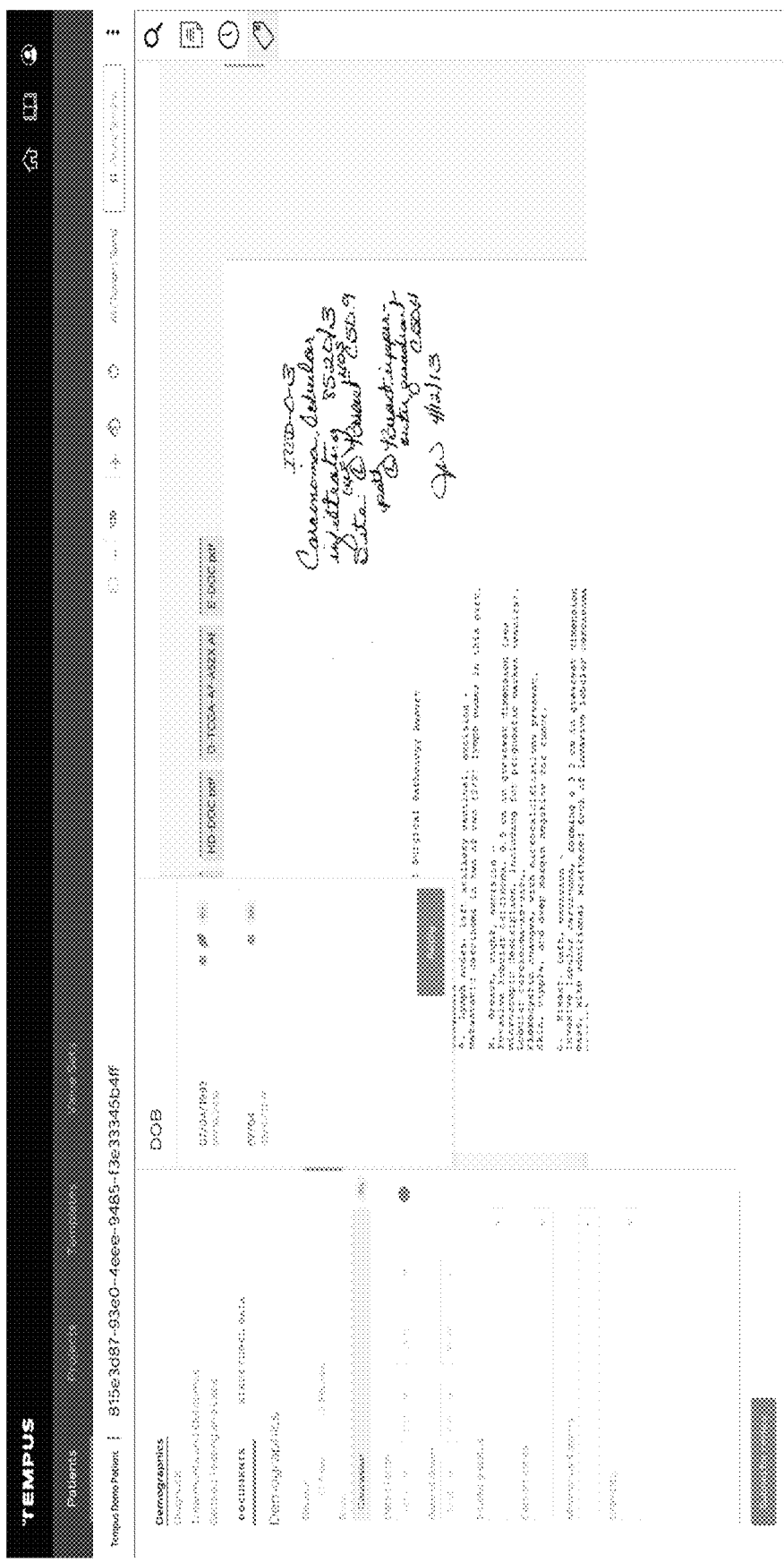
FIG. 13 depicts another exemplary user interface.
Figure 15:
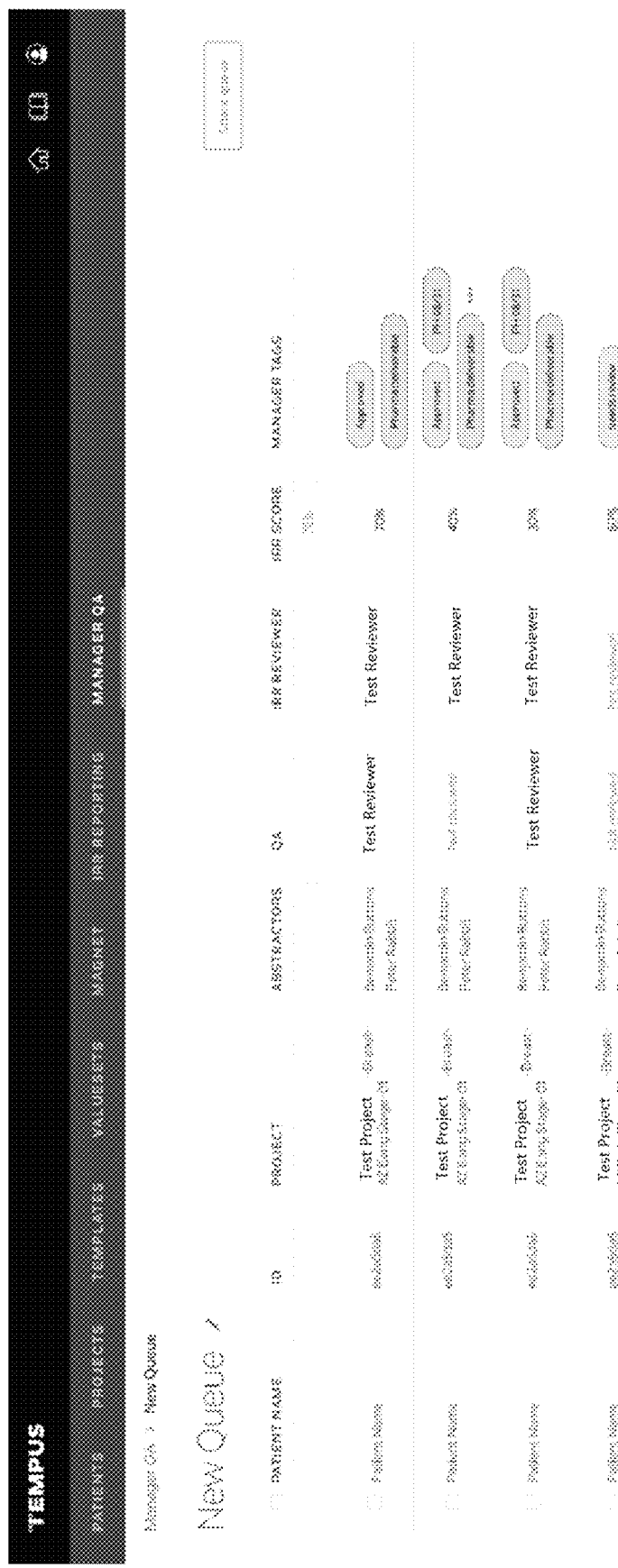
FIG. 15 depicts one example of various metrics or reports generated by the present system.

In another aspect, FIGS. 13 and 14 show a second exemplary user interface that a clinical data analyst may utilize to compare, merge and generate a "single source of truth" patient record across multiple data schemas, sources and/or streams.

Turning now to FIGS. 15-18, the system additionally may output and/or deliver various metrics and reports that provide insight into the accuracy and/or completeness of patient clinical records specific to a project as well as across selected projects for comparative and benchmarking purposes. Reporting data may include rankings and scores at both the patient record and clinical data attribute/field grain, indicative of data source/stream quality, completeness and integrity. This information becomes available to clinical data abstractors within a data curation, abstraction, and/or structuring toolset and user interface to aid in their desire to generate a "single source of truth" consolidated patient record atop various sources. It can also be used by clinical data managers to ensure a high quality data product deliverable for partners. As seen in these figures, the system may generate outputs permitting a user to visualize the IRR scoring and conflict resolution processes, as well as to review the subsequent reporting and insights generated afterwards. Additionally, a sample visualization describing data quality across various clinical data attributes and types is included for reference.

Figure 17:
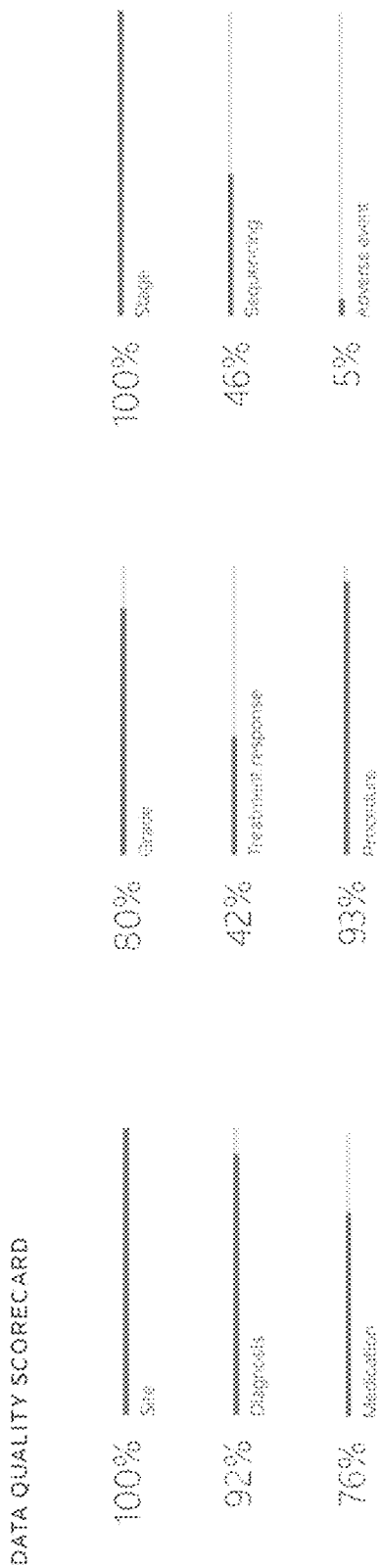
FIG. 17 depicts a third example of various metrics or reports generated by the present system.
Figure 18:
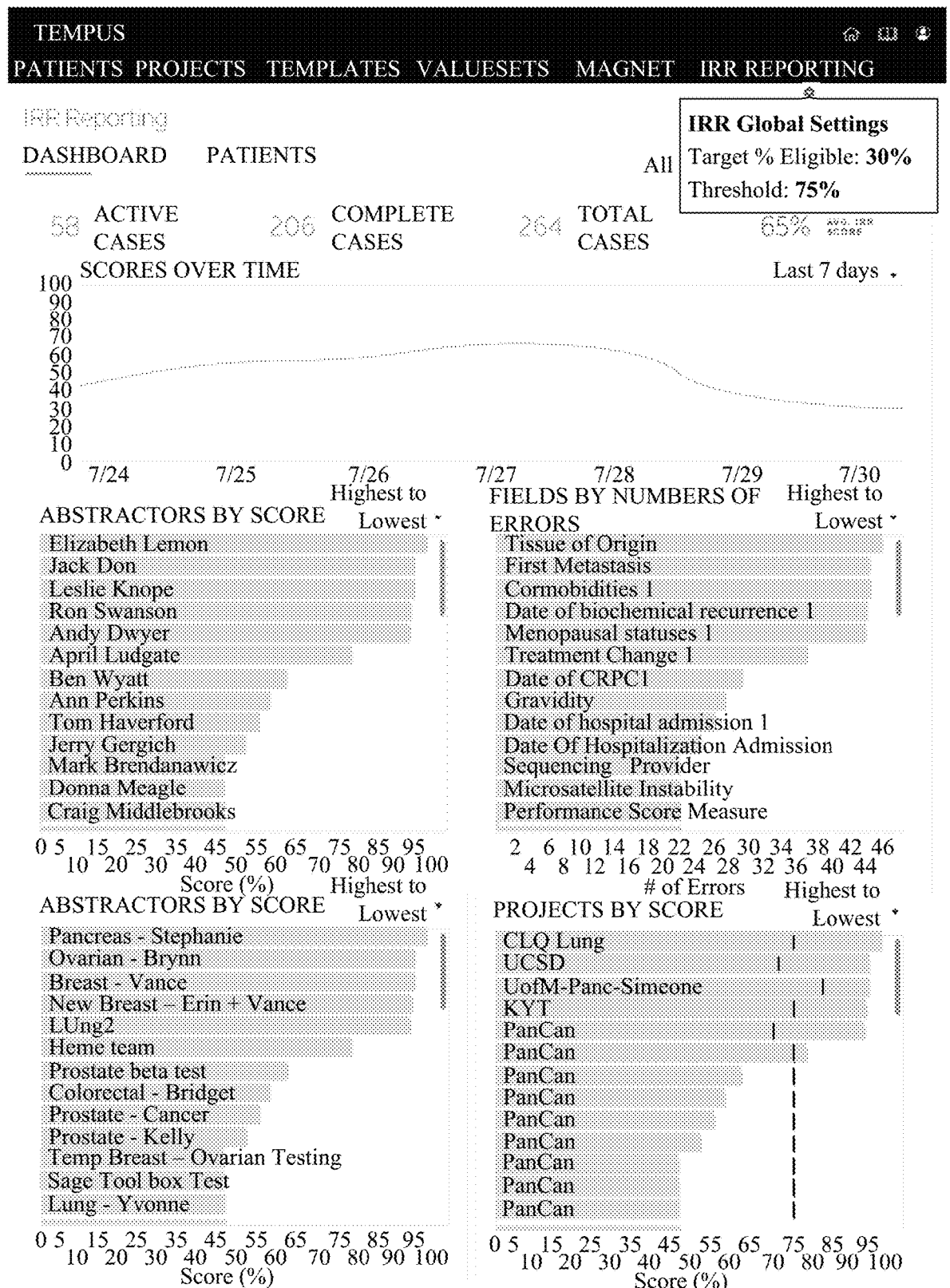
FIG. 18 depicts a fourth example of various metrics or reports generated by the present system.

With regard to the analytical tools described above, validation rules may be composed of hard, blocking errors (e.g., an indication of a new problem emerging after a recorded date of death) and loose warning notifications (e.g., an indication from one portion of the patient's record that the patient has stage 2 lung cancer while a second portion of the record indicates that the cancer is stage 3) that help to improve the integrity of a patient record during the clinical data structuring process as well as afterwards during subsequent QA activities. These validation rules can have various severity levels that indicate to an application and/or system process whether to reject fully or accept but call attention to a particular issue found in the data analyzed. Because the system may include a "sliding scale" of error severity, the results of the data quality tests may not be an "all-or-nothing" situation. Instead, as seen in FIG. 17, the system may generate quantitative metrics such as a "% success" indicator to measure the accuracy of the data structuring. This indicator also may account for the fact that a test suite may comprise dozens, if not hundreds, of different validation checks and that some may return acceptable results while others may indicate errors, missing information, or incomplete information.

Figure 19:
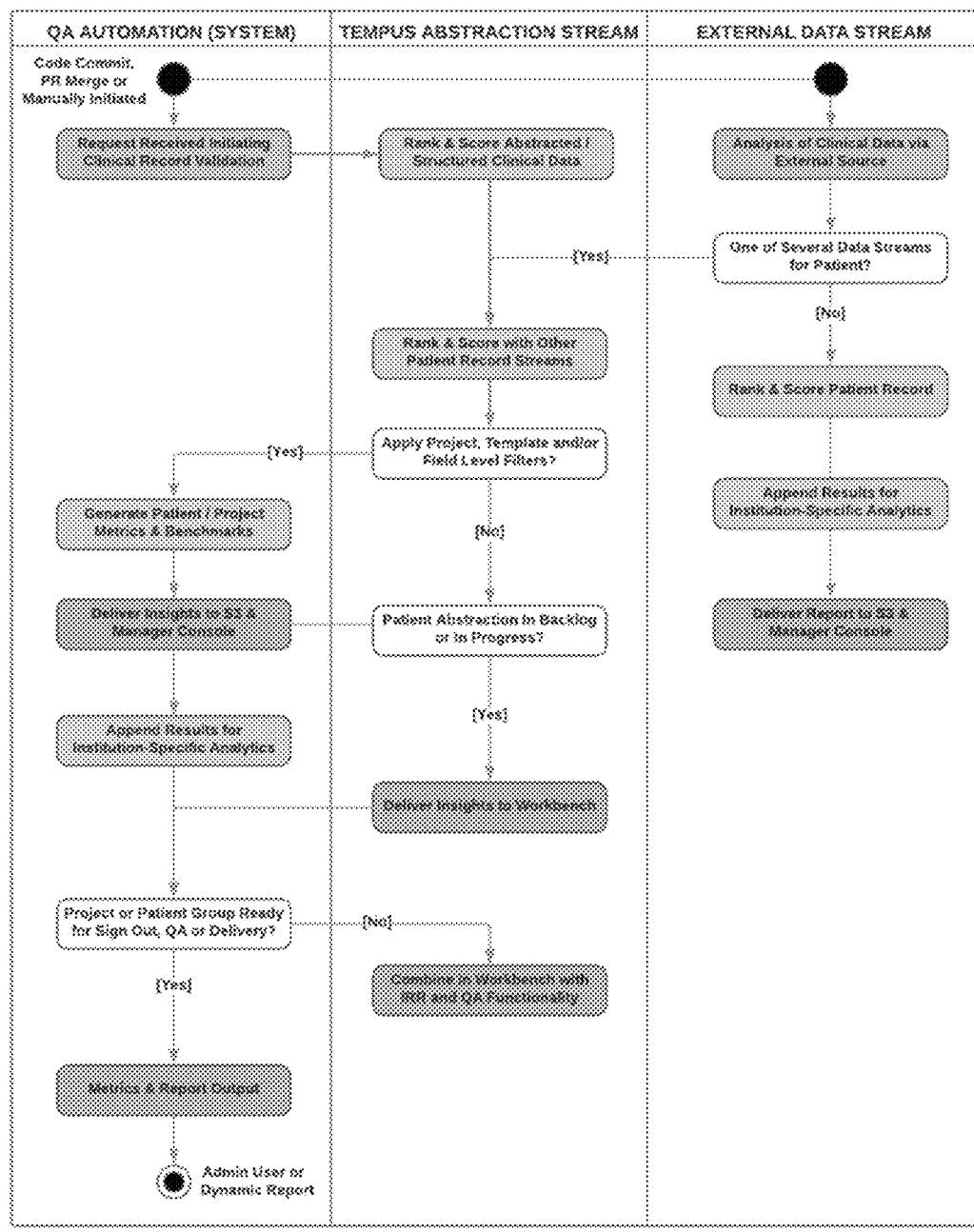
FIG. 19 reflects a generalized process flow diagram for carrying out the method disclosed herein, from raw data importation, through data structuring, and then through automated quality assurance testing.

Finally, FIG. 19 depicts one exemplary process flow of the present disclosure. In that figure, external data is received by the system, where it is ranked, scored, or otherwise structured, either on its own or in consideration with other data streams from the same patient. The structured data then is run through one or more QA Automation processes, such as the processes discussed herein in order to generate metrics and reports that can be output, e.g., to an administrative user or to the institution providing the external data.

In addition to the details of data acquisition, structuring, analytical triggering, and post-trigger analysis for a plurality of different use cases set forth herein, other relevant details of those actions may be found in the commonly-owned U.S. patent application Ser. No. 16/657,804, titled "Data Based Cancer Research and Treatment Systems and Methods," filed Oct. 18, 2019, the contents of which are incorporated herein by reference in their entirety.

While the invention may be susceptible to various modifications and alternative forms, specific embodiments have been shown by way of example in the drawings and have been described in detail herein. However, it should be understood that the invention is not intended to be limited to the particular forms disclosed. Thus, the invention is to cover all modifications, equivalents, and alternatives falling within the spirit and scope of the invention as defined by the following appended claims.

What is claimed is:

1. A method for checking the quality of data content in a structured clinical record, comprising:
    ingesting data from a plurality of electronically stored data sources, the data sources comprising unstructured or differently-structured data;
    structuring the data from the plurality of data sources to generate a structured clinical record;
    in response to a triggering event selected from among a plurality of different triggering events occurring, providing a data quality test that checks the content of at least a portion of the data content in the structured clinical record and determining whether the at least a portion of the data content is structured according to a scheme in which the at least a portion of the data content includes a data value for each data element and the data value for each data element is mapped to an accepted medical concept, the data quality test identifying which data elements within the portion of the data content to evaluate and which validation rules or checks to apply to the data elements;
    applying a test suite encoded with the data quality test to the at least a portion of the data content, and determining whether the portion of the data content is structured according to the scheme, the test suite selected from among a plurality of possible test suites, wherein the test suite comprises a genetic testing test suite, and wherein the data quality test within the genetic testing test suite further includes molecular variant criteria comprising identifying a gene and a type of molecular variant of the gene;
    returning the results of the data quality test; and
    when the results of the data quality test indicate that the evaluated data elements are accurately structured within a threshold level, providing a copy of the portion of the data content to one or more recipients, the copy comprising the evaluated data elements,
    when the results of the data quality test indicate that the evaluated data elements are not accurately structured within the threshold level,
        receiving a modification associated with a structure of the portion of the data content,
        restructuring the portion of the data content based on the modification such that the portion of the data content is accurately structured according to the scheme, and
        providing the restructured portion of the data content to the one or more recipients.

2. The method of claim 1, wherein the structured clinical record includes a diagnosis date and a diagnostic test date, and the data quality test checks if the diagnostic test date is prior to the diagnostic date.

3. The method of claim 1, wherein:
    the structured clinical record includes genetic testing results, and
    the data quality test includes a data sufficiency criterion that checks if the genetic testing results are complete.

4. The method of claim 1, wherein the results of the data quality test are returned in a "% success" format.

5. The method of claim 1, further comprising:
    updating the structured clinical record data in response to the results.

6. The method of claim 1, wherein the step of applying the data quality test to the portion of the data content is performed in response to an on-demand request from a user initiating the data quality test to the portion of the data content.

7. The method of claim 1, wherein the step of applying the data quality test to the portion of the data content is performed in response to initiating the data quality test via a background service.

8. The method of claim 7, further comprising:
    making, reviewing, and approving new code commits capturing modifications to the data quality test; and
    merging the new code commits into one or more code branches for subsequent application build phases.

9. The method of claim 1, further comprising:
    receiving and processing additional structured data;
    applying the data quality test to the additional structured data; and
    returning the results of the data quality test applied to the additional structured data.

10. The method of claim 9, wherein the receiving and processing steps automatically trigger the applying step.

11. The method of claim 9, wherein the data quality test includes evaluating the additional structured data relative to other patient record data received via other sources.

12. The method of claim 11, wherein the additional structured data is checked by the data quality test or a different data quality test.

13. The method of claim 1, wherein the data quality test checks the content of at least a portion of the data content in the structured clinical record against clinical attributes required for inclusion in or exclusion from a clinical trial; and
    determining eligibility of the patient for the clinical trial based in part on the results of the data quality test.

14. The method of claim 1, comprising:
    receiving and structuring unstructured data substantially in real time as it is being entered by a user into the clinical record,
    wherein the portion of the data content comprises the resulting structured data.

15. The method of claim 14, wherein the returning step includes informing the user of errors or incomplete information in the unstructured data.

16. The method of claim 15, further comprising:
    receiving revisions to the unstructured data substantially in real time from the user; and repeating the structuring, initiating, and returning steps to determine whether the errors or incomplete information have been corrected.

17. The method of claim 1, wherein the structured clinical record is stored in an electronic health record.

18. The method of claim 1, wherein the data quality test comprises a cancer diagnosis criteria.

19. The method of claim 1, wherein the data quality test comprises a date of cancer diagnosis criteria.

20. The method of claim 1, wherein the data quality test comprises a metastatic cancer diagnosis criteria.

21. The method of claim 1, wherein the data quality test comprises a date of recurrence criteria.

22. The method of claim 1, wherein the data quality test comprises a staging criteria.

23. The method of claim 1, wherein the data quality test comprises a medication criteria.

24. The method of claim 1, wherein the data quality test comprises a tumor mutational burden criteria.

25. The method of claim 1, wherein the data quality test comprises a microsatellite instability criteria.

26. The method of claim 1, wherein the data quality test comprises a PARP inhibitor criteria.

27. The method of claim 1, wherein the data quality test comprises a gender criteria.

28. The method of claim 1, wherein the step of identifying a gene and a type of molecular variant comprises identifying the gene from among a plurality of possible genes.

29. The method of claim 1, wherein the step of identifying a gene and a type of molecular variant comprises identifying the type of molecular variant from among a plurality of possible variants.

30. The method of claim 1, wherein the step of determining whether the portion of the data content is structured into a scheme comprises determining whether the identified gene and type of molecular variant correspond to a proper combination of gene and type of molecular variant.

* * * * *